United States Patent [19]

Lin

[11] Patent Number: 5,692,609
[45] Date of Patent: Dec. 2, 1997

[54] STORE BOX FOR DENTAL EQUIPMENT

[76] Inventor: Jyh-Sheng Lin, 184, Ching-Yun Rd., Tuu-Cherng, Taipei Hsien, Taiwan

[21] Appl. No.: 758,776
[22] Filed: Dec. 3, 1996
[51] Int. Cl.$^6$ ................................................ A61C 19/02
[52] U.S. Cl. .................. 206/368; 206/762; 206/379; 433/77; 433/79
[58] Field of Search ........................... 206/379, 368, 206/369, 63.5, 443, 762, 765, 756; 433/77, 79

[56] References Cited

U.S. PATENT DOCUMENTS

| | | | |
|---|---|---|---|
| 2,403,825 | 7/1946 | Nissenbaum | 206/379 |
| 4,356,918 | 11/1982 | Kahle et al. | 206/762 |
| 4,930,660 | 6/1990 | Porteous | 206/63.5 |
| 4,959,199 | 9/1990 | Brewer | 206/63.5 |
| 5,332,392 | 7/1994 | Bierbaum et al. | 433/79 |

FOREIGN PATENT DOCUMENTS 529132  3/1993  European Pat. Off. ............. 433/77

*Primary Examiner*—Paul T. Sewell
*Assistant Examiner*—Anthony Stashick
*Attorney, Agent, or Firm*—Birch, Stewart, Kolasch & Birch, LLP

[57] ABSTRACT

The present invention relates to a storage box for dental equipment, comprising a box and a cover which are joined together with pivotal parts; a chute is made on the box and laid with a plurality of check plates; along the close end the check plate, has a plurality of hopper type slots interweaving with the check plates; the slots may hold the drilling/filing needles which are separated by these check plates, and head end of each needle is projecting over the check plate in facility of chucking up the needle with the clip; the open end of the cover may receive the contact side of the notch, when the cover is open from the box it may be turned to the bottom of the box and holding up the back of the box so that the box may be leaning inclined upon the notch of the cover to ensure that drilling/filing needles are securely placed in the box.

2 Claims, 2 Drawing Sheets

STORE BOX FOR DENTAL EQUIPMENT

The present invention relates to a box for holding dental equipment, and particularly to a store box for personal dental equipment so as to facilitate the use of dentist.

Recently because of increasing number of AIDS, both medical personnel and patients have felt a strong wave of plague. As AIDS has been evidenced to infect by means of blood or sperm, medical personnel who are exposed to high risk have taken various protections to prevent from infection as a result of careless treatment. In addition, non-AIDS patients are also afraid of being exposed to AIDS infection during the treatment so they want medical facilities to use disposal needle or personal medical equipment so as to avoid AIDS infection. Owing to the influence of anti-AIDS wave, now most of major hospitals have selected disposal needles and dentists have also placed stress on using personal dental equipment to relieve patients from fear of AIDS infection.

Though popular application of personal dental equipment in the dental circle has become the most basic reference to the patients for the selection of dental treatment, so-called personal dental equipment applies to a set of dental equipment solely for personal purpose only, not available for any other person. Though a set of personal dental equipment may prevent infection by sharing with others, the personal dental equipment must be thoroughly sterilized after use so as to meet sanitary requirement.

The existing method of sterilization of dental equipment is to use a metal box for holding dental equipment desired for sterilizing and to achieve such goal by placing in a high temperature or high cycle wave environment. In general, equipment for sterilizing personal equipment should be sterilized respectively so as to meet sanitary requirement but most of hospitals have sterilized such equipment in batch manner so as to save manpower and material resource. Though this way has not met the requirement of individual sterilization mutual contamination between the equipment due to incomplete sterilization may be reduced if they could be separated from each other during sterilization. Nevertheless, owing to the sake of manpower and material saving, there are many hospitals or clinics which have failed to fulfill the sorting task to cause identification problem of medical equipment after sterilized. Such a way of sterilizing without sorting has caused the use of personal equipment useless.

The existing sterilization of all equipment in one metal box has caused a great trouble to the use of "drilling needle" or "filing needle" for filling/or tooth-root treatment. The reason is because the volume of drilling needle or filing needle is very small so it has to be picked with clip for mounting on the bit. For sterilizing, if these needles were all placed in a metal box, needles of right size should be identified with effort and selected for use after sterilized as in the past the doctors had to search the needles in a lunch box after sterilized. Because there are various sizes of drilling or filing needles and some specific sizes are usually used only, search not only may cause a delay of treatment but also may cause choosing a wrong size from such a search.

In view of collective sterilization of dental equipment in a metal box mentioned above to cause mutual contamination due to incomplete sterilization and trouble to the use of small equipment such as drilling or filing needles, the inventor therefore, based on his clinical experience as a dentist over the years, has designed a box available for open/close and with a plurality of sector blocks which may hold drilling and filing needles in clear and good manner in facility of picking for use. When the cover of the box is open it may be turned to the bottom of the box to form an inclined pod for the box to be held so that the present invention may be securely placed on the bracket table in facility of the dentist to find the right drilling or filing needle at the most effective angle within the shortest period. Another feature of the present invention lies in the box which may store drilling and filing needles all in one. Because it is made from heat-resistant material, it together with needles can be sent in for sterilizing to meet sanitary requirement of personal equipment.

DETAILED DESCRIPTION OF PREFERRED EMBODIMENT

Figure 1:
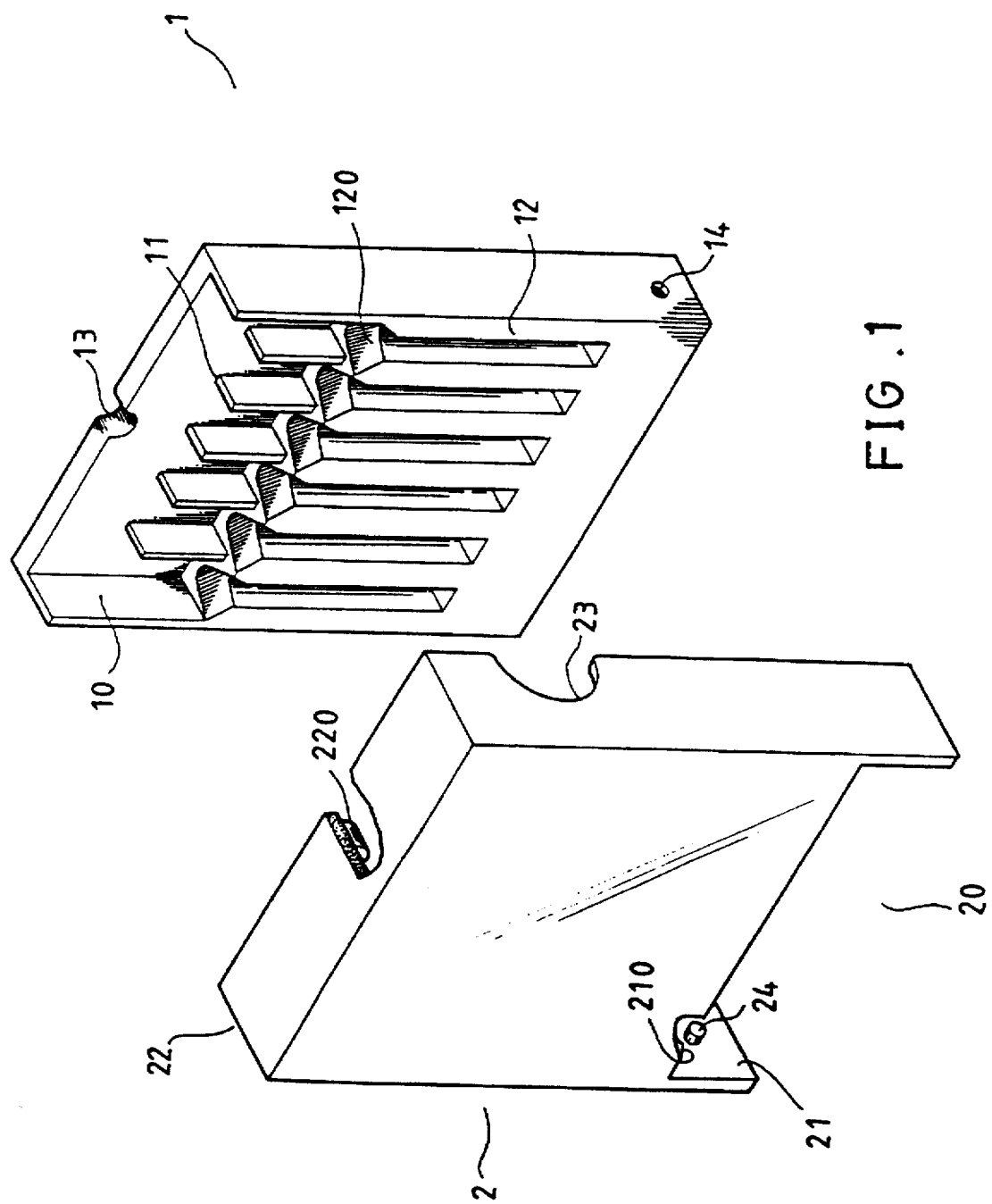
FIG. 1 is an exploded-elevational view of the structure of the present invention.

Referring to FIG. 1, the present invention comprises a box body 1 and cover 2; wherein said box body having a chute 10 near the upper end. and said chute having check plates 11 therein; said check plates 11 downwardly having a plurality of hopper type slots 12, and said slots interweaving with said check plates. and according to a front view the slot mouth 120 resembling an upward opening and according to a top view it resembling an outward opening; further in the top center of chute 10 having a setting groove 13, and the bottom end of each side of box body 1 having pivotal hole 14; said cover 2 having volume little greater than said box 1 and having an open side 20: said open side 20 having a notch 21, and distal end of said notch having a bevel contact side 210; a close side 22 against the open side having a setting buckle 220; near upper end of each side of the cover having a notch 23, and having a pivotal point 24 near the open side 20.

Figure 2:
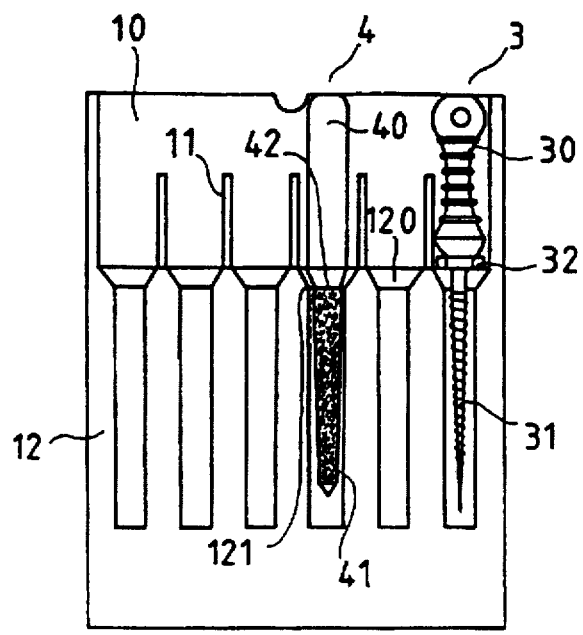
FIG. 2 is an embodiment of the present invention showing the box is holding drilling needles and filing needles respectively.

Referring to FIG. 2, the box 1 may be provided for holding filing needle 3 and drilling needle 4; said filing needle 3 is loaded with its flange 32 between its head end 30 and tail end 31 on the top of the slot mouth 120 of hopper type slot 12 whereby head end 30 of filing needle is loaded between the two check plates of the chute 10, and tail end 31 is loaded in the hopper type slot 12; the head end 40 and tail end 41 of drilling needle 4 are loaded in the chute 10 and hopper type slot 12 respectively, and downward-reducing neck 121 of slot mouth 120 is setting with adjacent neck 42 of head end 40 and tail end 41 of drilling needle to allow the drilling needle 4 for loading in the box. Therefore, the box 1 may hold the filing needle 3 and drilling needle 4 of different shape.

Figure 3:
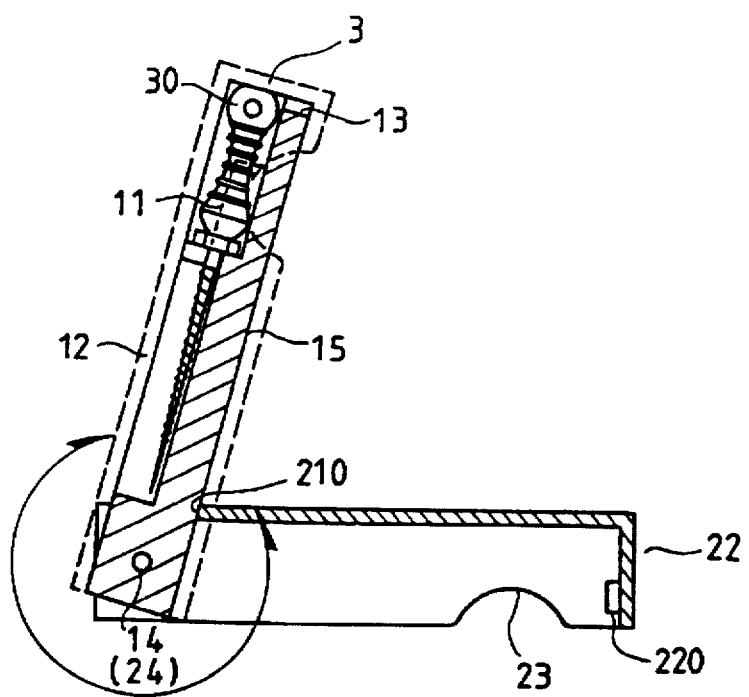
FIG. 3 is a schematic drawing, showing the status of the embodiment.

Referring to FIG. 3, the assembly of the present invention is achieved by means of fastening the pivotal point 24 on the open side of cover 2 into the pivotal hole 14 on each side of the box 1; dotted line means the cover 2 is put on the box 1; when the cover 2 is put on the box 1, it may limit the filing needle 3 or drilling needle 4. The cover 2 is open and turned to the bevel contact side 210 of the notch 21 till holding up the back 15 of the box 1 so that the box 1 may be located in the notch 21 with the support of bevel contact side 210; when said cover 2 is open from the box 1, the chute 10 on the upper end of the box 1 may allow the top space of filing needle 3 or drilling needle 4 in facility of user to take it directly from the top end of the chute 10. The height of check plates 11 in the chute 10 should not exceed the top end of drilling and filing needles. Part of drilling and filing needles may break off the limit of the left and right check plates 11 so as to take the drilling and filing needles from the top end or front side of the box easily; though the check plate 11 is provided for separating and arranging the drilling and filing needles in straight manner, however the thickness of check plate 11 results in a seam formed between two drilling/filing needles to facilitate the clip stretching into it for chucking the drilling/filing needle.

Referring to FIG. 3, upon completion of use of drilling and filing needles when the cover 2 is put on the box 1 and the buckle 220 of the cover 2 is setting with the setting slot 13 of the box 1, the two can join together; the notch 23 on each side of the cover 2 is provided in facility of fingers to hold each side of the box 1 to form an ideal point for applying force when the cover 2 is open, and to allow the box 1 for leaning inclined on the bevel contact side 210 of the cover 2, and drilling, filing needles in the box 1 may therefore be placed in secure manner because the box appears bevel, and this may allow the dentist to chuck up the equipment desired for use without risk of falling down to the floor. Further as the volume of the cover 2 is little greater than the box 1 the cover 2 when turned open may form a large and firm base. When drilling and filing needles are desired for sterilization, the present invention may be placed in the box directly for sending in sterilization whereby the equipment after sterilized may remain laid in the box in straight manner without mixing with other equipment in the box. Therefore the present invention is an ideal storage box suitable for personal dental equipment and the use of the dentist with convenience.

I claim:

1. A storage box for dental equipment, comprising a box and a cover wherein:

said box having a chute near its end portion, said chute having a plurality of check plates arranged at equal distance; said check plate downwardly having a plurality of hopper type slots, and said check plates interweaving with said slots, and the slot mouth resembling top-to-bottom and external-to-internal gradual-reducing hopper; the chute having a setting groove at the open end, and each side of box having a pivotal hole near the close end;

said cover having an open side and volume little greater than the box; said open side cut with a section along the cover to form a notch, and the distal end of said notch forming a bevel contact side; the close side against the open side having a buckle, and each side of the cover having an open notch near the top end, and inside having left and right pivotal points near the open side;

said cover put on the box, pivotal points fastening into the pivotal hole of the box, and buckle of said cover setting into the groove of the box to join the cover with the box; the hopper type slots in the box available for holding the drilling/filing needles which are separated by check plates, and head end projecting over the chute to facilitate chucking up with the clip; upon opening the cover turnable to the close end of the box, and bevel contact side of the cover holding up the back of the box to enable the box to be leaning inclined upon the notch.

2. The storage box for dental equipment as claimed in claim 1 wherein the open notch of the cover when put on the box, fingers are allowed to hold the box through the notch in facility of applying force to open the cover from the box.

* * * * *